(12) United States Patent
Wright et al.

(10) Patent No.: US 8,827,959 B2
(45) Date of Patent: Sep. 9, 2014

(54) SECUREMENT DEVICE FOR CATHETERS

(75) Inventors: Clifford A. Wright, San Diego, CA (US); Robert F. Eisele, Carlsbad, CA (US); Thomas R. Jackson, La Jolla, CA (US)

(73) Assignee: Venetec International, Inc., Covington, GA (US)

( * ) Notice: Subject to any disclaimer, the term of this patent is extended or adjusted under 35 U.S.C. 154(b) by 455 days.

(21) Appl. No.: 12/532,133

(22) PCT Filed: Mar. 20, 2008

(86) PCT No.: PCT/US2008/057751
§ 371 (c)(1),
(2), (4) Date: Sep. 18, 2009

(87) PCT Pub. No.: WO2008/116119
PCT Pub. Date: Sep. 25, 2008

(65) Prior Publication Data
US 2010/0114034 A1     May 6, 2010

Related U.S. Application Data

(60) Provisional application No. 60/895,943, filed on Mar. 20, 2007.

(51) Int. Cl.
*A61M 5/32* (2006.01)
*A61M 25/02* (2006.01)

(52) U.S. Cl.
CPC ......... *A61M 25/02* (2013.01); *A61M 2025/024* (2013.01)
USPC .......................................................... 604/174

(58) Field of Classification Search
USPC ........................................ 604/174, 177–180
See application file for complete search history.

(56) References Cited

U.S. PATENT DOCUMENTS

| 4,389,754 | A | 6/1983 | Sohma |
| 4,416,664 | A | 11/1983 | Womack |
| 6,663,600 | B2 * | 12/2003 | Bierman et al. ............... 604/174 |
| 2002/0165493 | A1 * | 11/2002 | Bierman ........................ 604/174 |
| 2006/0058738 | A1 | 3/2006 | Ponzi et al. |

FOREIGN PATENT DOCUMENTS

| JP | 52-4691 | 2/1977 |
| JP | 63-501477 | 6/1988 |

* cited by examiner

*Primary Examiner* — Kevin C Sirmons
*Assistant Examiner* — Deanna K Hall
(74) *Attorney, Agent, or Firm* — Knobbe Martens Olson & Bear, LLP

(57) ABSTRACT

A system for securing a medical device such as a catheter or other medical article having various shapes or sizes in place on a patient includes a securing device. The securing device may optionally include a retainer having one or more receiving areas and one or more retention arms adjacent to the receiving areas. The securing device may also include a retention strap having a latching element that is removably connectable to a retention arm to securely hold a catheter in place. The retainer may optionally be connected to a base which may optionally be connected to an adhesive pad for easy attachment of the securing device to a patient.

10 Claims, 20 Drawing Sheets

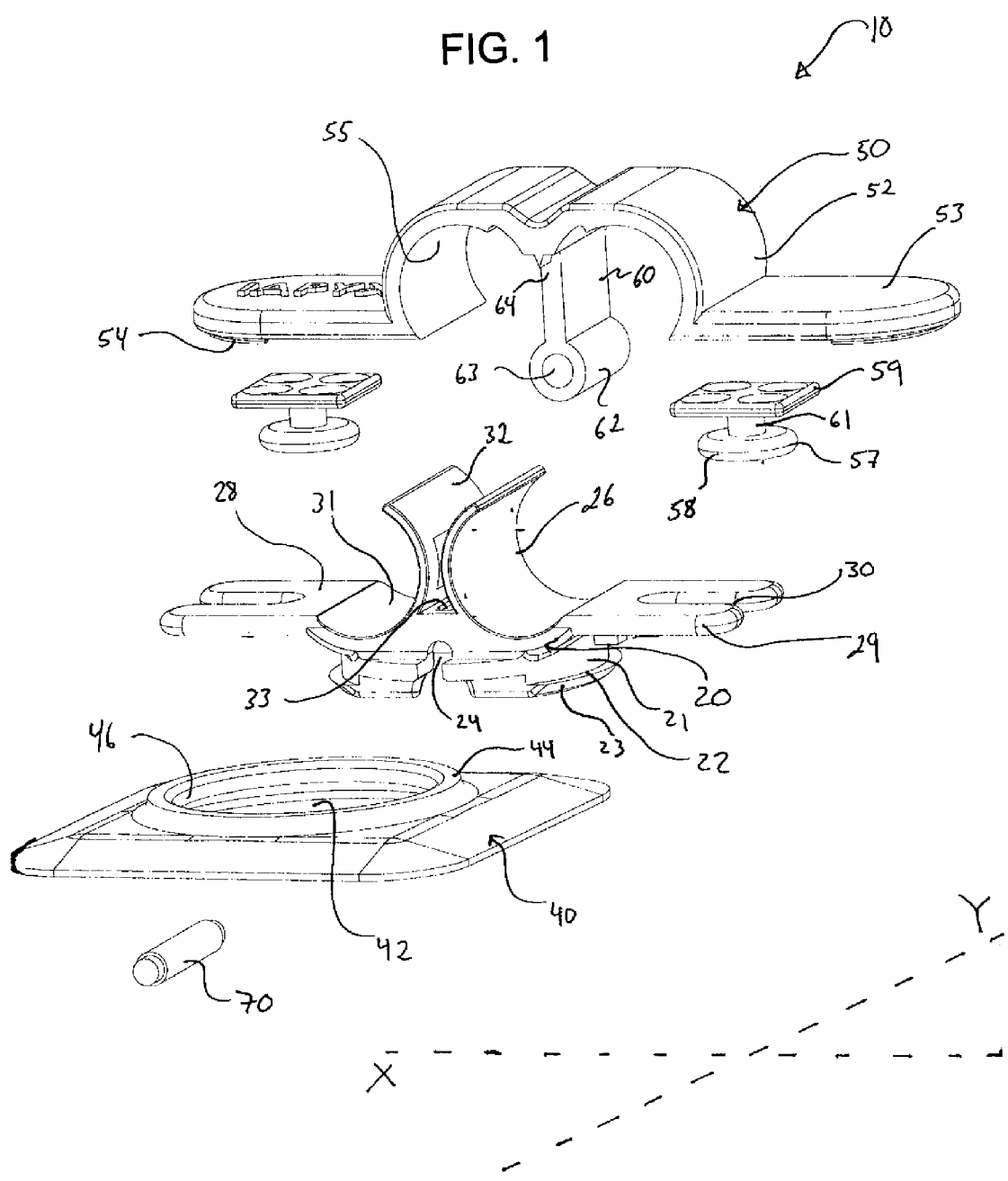

SECUREMENT DEVICE FOR CATHETERS

CROSS-REFERENCE TO RELATED APPLICATIONS

This application is the National Stage of International Application No. PCT/US2008/057751, filed on Mar. 20, 2008, entitled SECUREMENT DEVICE FOR CATHETERS, which claims the benefit of U.S. Provisional Patent Application No. 60/895,943, filed Mar. 20, 2007, both of which are hereby expressly incorporated by reference in their entireties.

BACKGROUND

It is often necessary to drain fluids from a patient or introduce liquid medications directly into a blood vessel of a patient. For longer term and more specialized needs, catheters or other devices are used. A catheter is typically a tube inserted through an orifice in the body or through an incision in the skin into a blood vessel in the patient's body, generally without surgery. A Foley catheter is a type of catheter that is inserted through a patient's urethra and into the bladder to drain urine from patients that are incontinent, bed ridden, or otherwise unable to urinate on their own.

Various catheters may remain in place in a patient for several weeks or months. It is important that movement of the catheter be minimized. If the catheter is not secured in place, it may be inadvertently displaced from the intended location or moved back and forth (pistoning), resulting in irritation or disruption of fluid or urine drainage from a patient or in disruption of proper introduction of medications to the patient. This can increase the potential for infection or bleeding at the catheter insertion site. If extensive movement occurs, the catheter could even come out of the patient, requiring re-insertion, often with hospitalization.

In the past, catheters were simply taped into place on the patient's skin. However, taping is time consuming and labor intensive. Tape also collects bacteria and must be frequently removed and replaced. More importantly, taping is not necessarily effective in securing a catheter in place. Sutures have also been used to attach a catheter to a patient. With sutures, the catheter is stitched onto the skin. Sutures, however, can also be a source of infection, can cause pain and inflammation, and can make it more difficult to clean around the incision site. Sutures also require time and skill to place, and can cause scarring.

More recently, manufactured catheter anchors or securing devices have come into more widespread use. These devices are designed to secure specific catheters in place. While various designs have been used, these devices generally have an adhesive-backed pad that bonds to the skin over a large area. The catheter is secured into or onto a catheter anchor designed for holding the catheter. These anchoring devices have various advantages over tape or sutures. However, engineering design challenges remain in providing reliable, secure, and efficient anchoring devices. For example, existing anchoring devices are generally designed for only a specifically sized or shaped catheter. As a result, in a hospital or clinic setting, multiple anchors may be needed to accommodate use of different types of catheters. This adds to the cost and complexity of sourcing, inventory, storage, and selection of the anchoring devices. Accordingly, improved anchoring devices are needed which accommodate a variety of catheters and securely hold the catheters in place.

SUMMARY

A system for securing a medical device in place on a patient includes a securing device which may be used for securing a catheter, tube, or other medical article having various shapes or sizes to a patient. The securing device may optionally include a retainer with one or more receiving areas and one or more retention arms adjacent to or extending from the receiving areas. The securing device may also include a retention strap removably connectable to the retention arms. The retention strap may include one or more strap arms having one or more latching elements which are removably connectable to the retention arms to securely hold a catheter in place. The retainer may optionally be connected to a base which may optionally be attached to an adhesive pad for easy attachment of the securing device to a patient.

Other features and advantages will appear hereinafter. The features described above can be used separately or together, or in various combinations of one or more of them.

BRIEF DESCRIPTION OF THE DRAWINGS

In the drawings, wherein the same reference number indicates the same element throughout the views:

FIG. 1 shows an exploded front perspective view of a securing device, according to one embodiment, including a retention strap, a retainer, and a base.

DETAILED DESCRIPTION

Figure 2A:
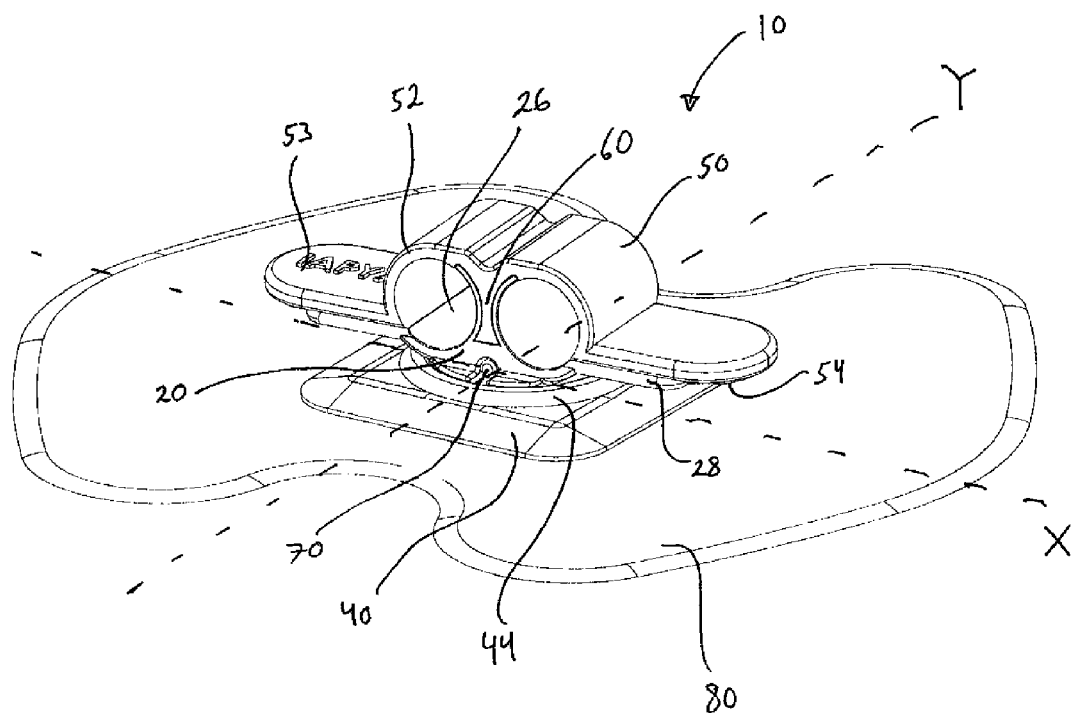
FIG. 2A shows a front perspective view of the securing device shown if FIG. 1, with the retention strap fastened to the retainer and the retainer connected to the base.

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

A device for securing a catheter or catheter fitting of various designs, shapes, and sizes includes a retainer and a retention strap removably connectable to the retainer. The retainer is preferably connected to a base. The retainer may have one or more receiving areas and one or more retention arms. The retention strap, which may be flexible, resilient or stiff, is preferably connected to the retainer and preferably has at least one strap arm and at least one latching element connected to the strap arm. A catheter may be securely held between the retainer and retention strap when the latching element of the strap arm is fastened or attached to the retention arm. The securing device may be attached to the patient to securely hold the catheter in place. The catheter can be removed from the retainer by detaching the latching element from the retention arm, lifting a strap arm, and removing the catheter.

A catheter or catheter fitting having various designs, shapes, or sizes can be securely held by a single securing device according to the embodiments described herein and can be quickly and easily attached to or removed from a patient. The devices described herein may be used with, e.g., Foley catheters, PICC lines, IV catheters, heart catheters, J-loops, and various other articles. In addition to a catheter or catheter fitting, the present securing device may be used to secure other tubes, cables, wires, or various other medical devices.

Turning now in detail to the drawings, as shown in the embodiment of FIG. 1, a securing device 10 has a retainer 20. The retainer 20 may include a trunk 21 or some form of an attachment member. In this particular embodiment the trunk 21 is substantially circular in shape and an attachment lip 22 runs along the bottom perimeter of the trunk 21. The trunk 21 may be configured as any shape or design, e.g., square, rectangular, etc., that is suitable for attachment to a base 40. An angled surface 23 may be provided along the outer surface of the attachment lip 22. The trunk 21 or other region of the retainer 20 may also include a retention slot 24, groove, track or other opening, which preferably runs generally along the longitudinal axis (as identified by line Y) of the securing device 10. The retention slot 24 may optionally divide the trunk 21 into two halves that are substantially symmetrical along the longitudinal axis of the trunk 21. The retention slot 24 may extend for a length along the longitudinal axis of the trunk 21 equal to the diameter of the trunk 21, or for a length shorter than the diameter of the trunk 21. In another embodiment, the retainer 20 may include attachment walls or other structure or extensions or a trunk for connecting the retainer 20 to a base or other platform. Any attachment piece or trunk may optionally be a separate piece. In another embodiment, the retainer may extend directly from a base or platform as a single unitary piece or the retainer and base may be separate pieces.

As shown in FIG. 1, the retainer 20 may also have one or more receiving areas 26. The receiving areas 26 extend up from the trunk 21. The receiving areas 26 are configured or arranged to receive or hold various parts of a catheter or other device. The receiving areas 26 may have a substantially semi-circular or semicylindrical shape. In one embodiment, one or more receiving areas 26 have a generally arc-shaped perimeter measuring greater than 180°. Preferably, the receiving area 26 has a perimeter measuring about 190°-200°. In another embodiment, the perimeter of the receiving area 26 may measure about 195°. The perimeter of the receiving area 26 may, however, be less than 180°. Optionally, the receiving area may be any other shape or design suitable for holding or receiving a catheter or catheter fitting, e.g., rectangular, cubical, oval, etc. In other embodiments, the receiving areas may extend directly from a base or platform or be positioned on a trunk, base or platform.

Figure 3:
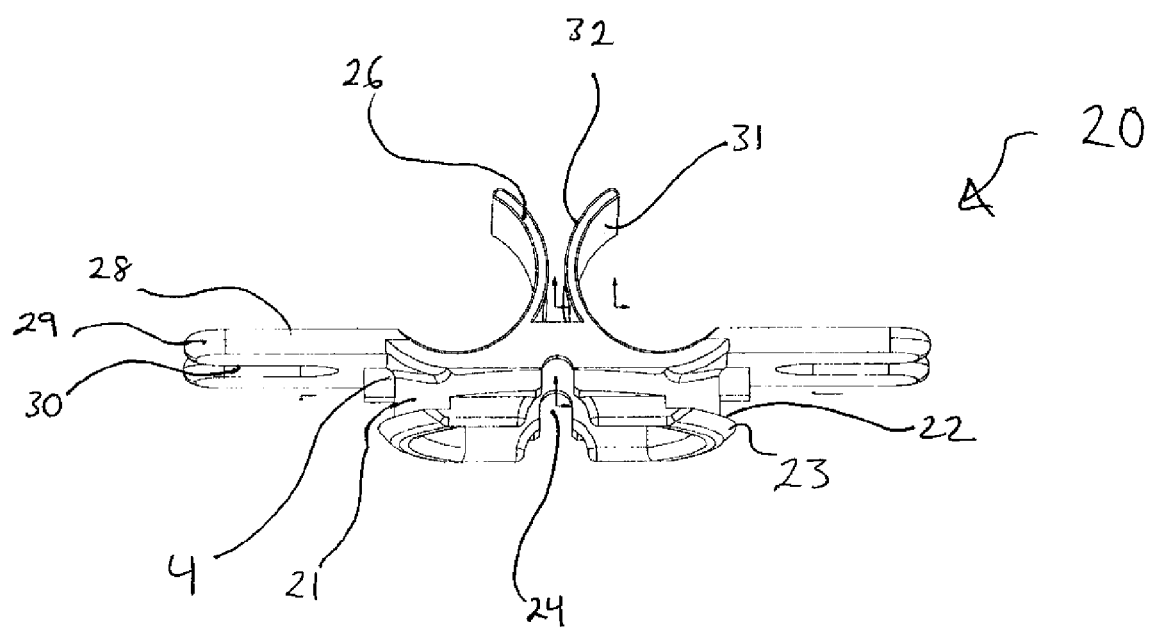
FIG. 3 shows a front perspective view of the retainer of the securing device shown in FIGS. 1 and 2A-2B.

The receiving areas 26 may include an inner concave surface 31 and an outer convex surface 32. As shown if FIGS. 1 and 3, the receiving areas 26 are arranged such that they sit adjacent to one another. At least a portion of the outer convex surface 32 of a first receiving area 26 facing at least a portion of the outer convex surface 32 of a second receiving area 26. Further, at least a portion of the inner concave surface 31 of the first receiving area 26 faces away from at least a portion of the inner concave surface 31 of the second receiving area 26 or at least a portion of the concave surface 31 may face away from the patient when the securing device 10 is attached to a patient. An opening 33 may be provided in between the two receiving areas 26 in the retainer 20. Thus, the receiving areas may be positioned slightly separated from each other, but optionally they may rest against each other. Optionally, the receiving areas may be a unitary or single piece, with the receiving areas extending in opposite directions of each other.

The receiving area 26 may run generally parallel to the longitudinal axis Y or at an angle, e.g., 1-45° to the longitudinal axis Y. Furthermore, a receiving area 26 may be arranged in an orientation such that the perimeter of the receiving area 26 is oriented from approximately one o'clock to nine o'clock, preferably from approximately one o'clock to eight o'clock. In other embodiments, the receiving area 26 may be arranged in an orientation such that the perimeter of the receiving area 26 is oriented from approximately three o'clock to nine o'clock.

In one embodiment, the retainer 20 may be made from a hard plastic, rubber, or silicone but other suitable materials may also be used to form the retainer 20. In certain embodiments, at least a portion of the perimeter of a receiving area 26 may be thinner than the remainder of the perimeter of the receiving area 26. Optionally, the receiving area 26 may be flexible throughout, the thinner portion may be more flexible than the thicker portion, or the thicker portion may be more flexible than the thinner portion, allowing the receiving area 26 to flex or expand to hold, receive, or restrain catheters or catheter fittings of various shapes or sizes. In one embodiment, the receiving area 26 may flex or expand outward to accommodate or receive a catheter, returning to its original position once the catheter is in place or removed. The receiving area 26 may be stiff or rigid or flexible and it may accommodate, hold, restrain or receive catheters or catheter fittings of various sizes or shapes either by itself or in combination with the retention strap 50.

The retainer 20 preferably includes at least one retention arm 28. As shown in an embodiment according to FIGS. 1 and 3, the retainer 20 includes two retention arms 28. The retention arms 28 each sit adjacent to a receiving area 26 and extend in substantially opposite directions, substantially perpendicular to the longitudinal Y axis of the securing device 10, or optionally at an angle, e.g., 1-45° to the longitudinal axis Y. The retention arms 28 may be substantially linear or flat. Provided at the end 29 of each retention arm 28 is a slot 30, groove, track or other opening. The slot 30 occupies at least a portion of the retention arm 28, in a direction substantially perpendicular to the longitudinal Y axis of the securing device 10, generally along the lateral X axis, or optionally at an angle, e.g., 1-45° to the longitudinal axis Y. Optionally, the retention arms may be positioned adjacent to, connected to or may extend from a receiving area, trunk, base or retainer.

Figure 2B:
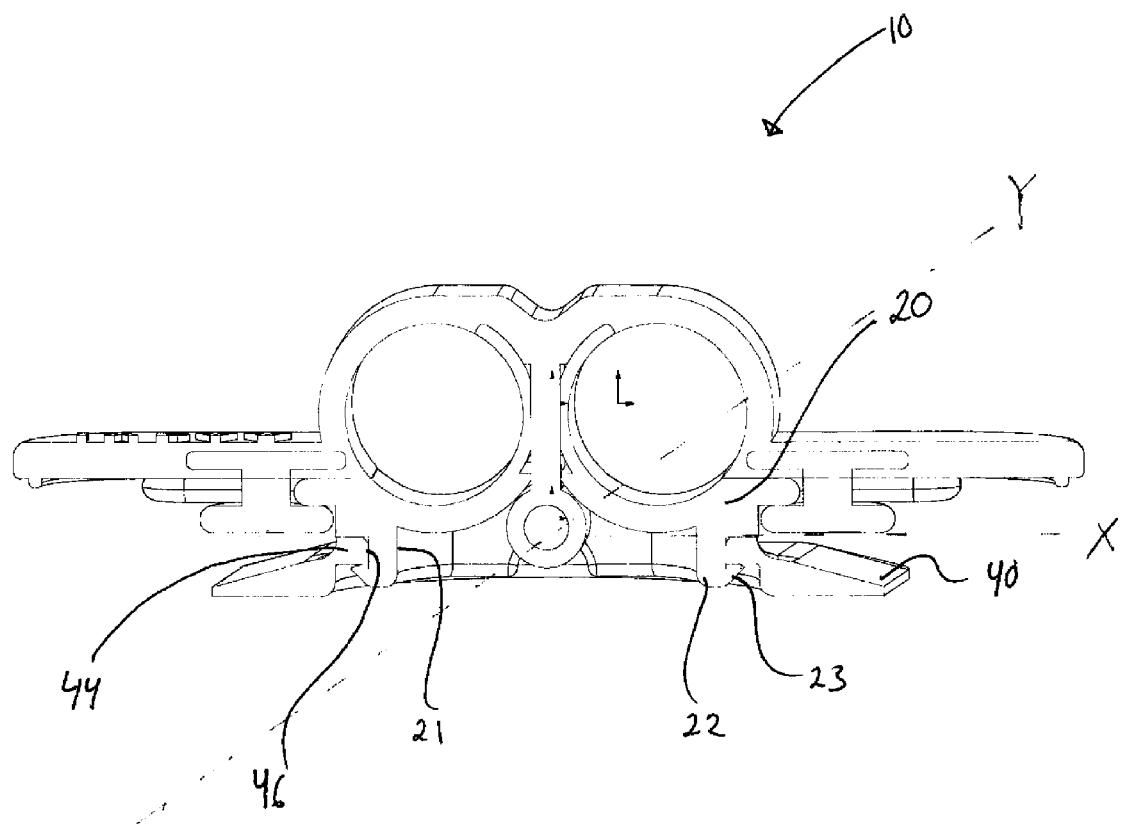
FIG. 2B shows a cross sectional view of the securing device shown in FIG. 2A, with a cross sectional plane running along the lateral X axis.

As further shown in FIGS. 1 and 2A-2B, the securing device 10 preferably includes a base 40 to which the retainer 20 is attachable. The base 40 may have a substantially flat, rectangular or square shape, or may be configured in any shape suitable for supporting the retainer 20 or being attachable to a patient. A receptacle 42 or other opening may be provided in the center of the base 40. A substantially circular ridge 44 may be located at the top end of the receptacle 42 including an inner surface 45. The inner surface 45 may or may not be angled. It is contemplated that the ridge 44 and the receptacle 42 could also have a shape other than circular, e.g., square, rectangular, or any shape suitable for receiving a retainer 20. The opening 33 between receiving areas 26 extends through the retainer 20 and the trunk 21 and is continuous with the receptacle 42. The base 40 is configured to receive the retainer 20, which may be removably or permanently attached thereto by any suitable method.

For example, as shown in FIGS. 1 and 2B, retainer 20 may be connected to the base 40 by engaging the optionally angled surface 23 of the attachment lip 22, against the inner surface 46 of the ridge 44 of the receptacle 42. As the retainer 20 is pushed into the receptacle 42 (typically the trunk 21 or some type of attachment member is pushed into the receptacle 42) of the base 40, the attachment lip 22 flexes or bends toward the center of the receptacle 42 as it slides against and past the inner surface 46 of the ridge 44. Once inside the receptacle 42 and past the inner surface 46 of the ridge 44, the attachment lip 22 flexes back to its original position, latching the retainer 20 into place and connecting it to the base 40.

The retainer 20 may be attached to the base 40 with a male-female attachment mechanism as described above. In another embodiment, the retainer 20 may be connected to the base 40 with a female-male attachment mechanism. That is, the attachment lip 22 and ridge 44 could be constructed such that an inner surface (which may or may not be angled) of the attachment lip 22 can engage against an outer surface of a ridge 44 (which may or may not be angled), and as the ridge 44 is pushed inside the trunk 21 and the attachment lip 22 slides over or past the ridge 44, the retainer 20 latches into place on the base 40. Other means for attaching the retainer 20 to the base 40 are also contemplated. For example, the retainer 20 may be fastened to the base 40 by being press fit or held together in place by friction. Alternatively, the retainer 20 and base 40 may include screwable thread for detachably fastening the retainer 20 to the base 40. Indeed, the base 40 and retainer 20 may be attached and configured in any manner suitable to allow for rotational or swivel movement between them. In another embodiment, the base and retainer may optionally be attached in a fixed relationship allowing for minimal or no movement between the two.

Figure 4A:
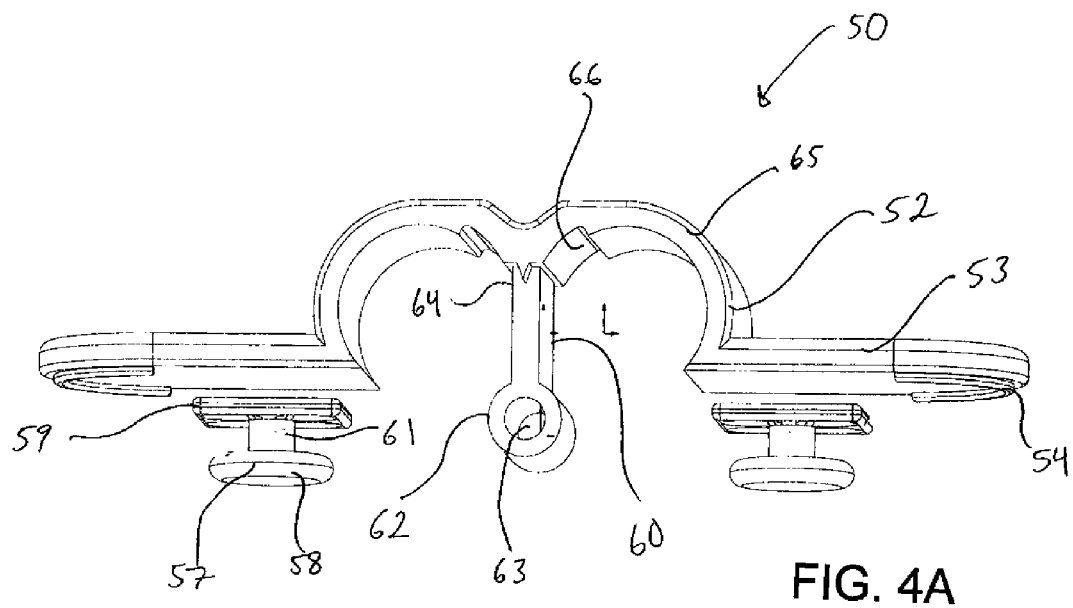
FIG. 4A shows an exploded front perspective view of the retention strap of the securing device shown in FIGS. 1 and 2A-2B.
Figure 4B:
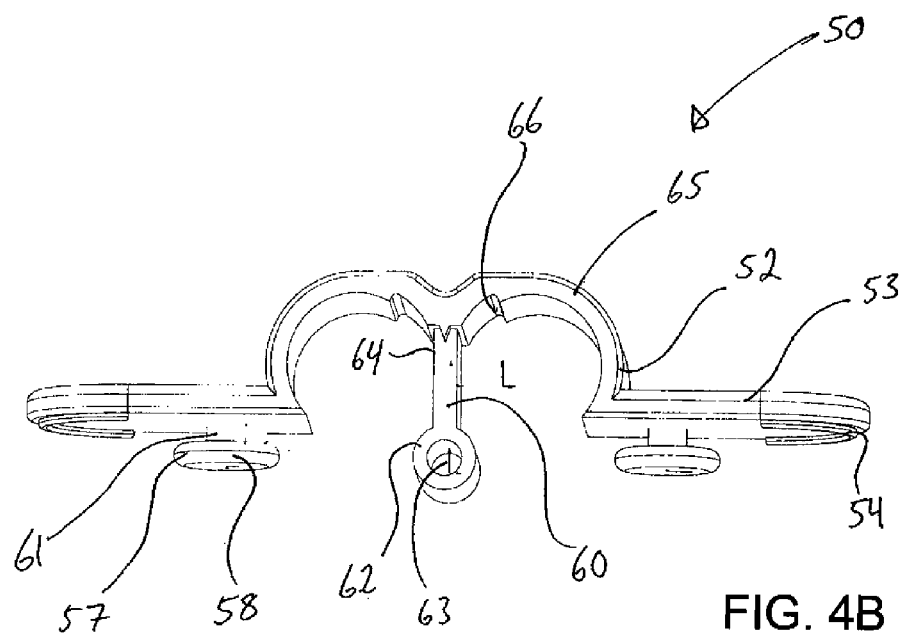
FIG. 4B shows a front perspective view of the retention strap shown in FIG. 4A.

With reference to FIGS. 1 and 4A-4B, the securing device 10 also preferably includes a retention strap 50. The retention strap 50 may be at least partially or generally flexible, elastic, or resilient and made from any suitable material (e.g., rubber, silicone, etc.) which allows the retention strap 50 to bend, stretch, or form around or over a catheter, catheter fitting, or other medical device of various shapes or sizes in order to securely surround or hold the device in place. Optionally, the retention strap 50 may be rigid or stiff. The retention strap 50 may have any dimensions (e.g., thickness, width, length, etc.) suitable to securely hold a catheter or other medical device of various shapes or sizes in place. The retention strap 50 may optionally include a central member 60. In one embodiment, a bottom end 62 of the central member 60 expands to form opening 63. The opening 63 may be configured to receive a pin 70 or any other insertable structure suitable for fitting within the retention slot 24 of the retainer 20 to facilitate attachment of the retention strap 50 to the retainer 20. This attachment prevents the retention strap 50 from being inadvertently pulled out of the opening 33 while the device is being used for catheter securement. The retention strap may be oriented such that the inner surface 55 of the retention strap 50 generally faces toward a patient's skin when the catheter device 10 is positioned on a patient.

Figure 5A:
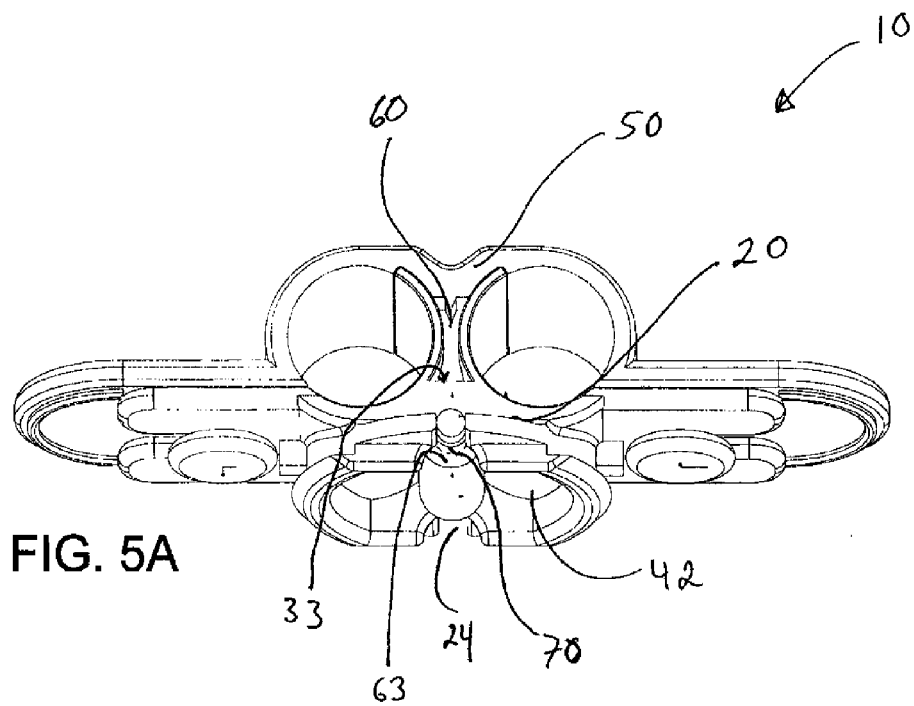
FIG. 5A shows a bottom perspective view of the securing device shown if FIGS. 1 and 2A-2B without the base.
Figure 5B:
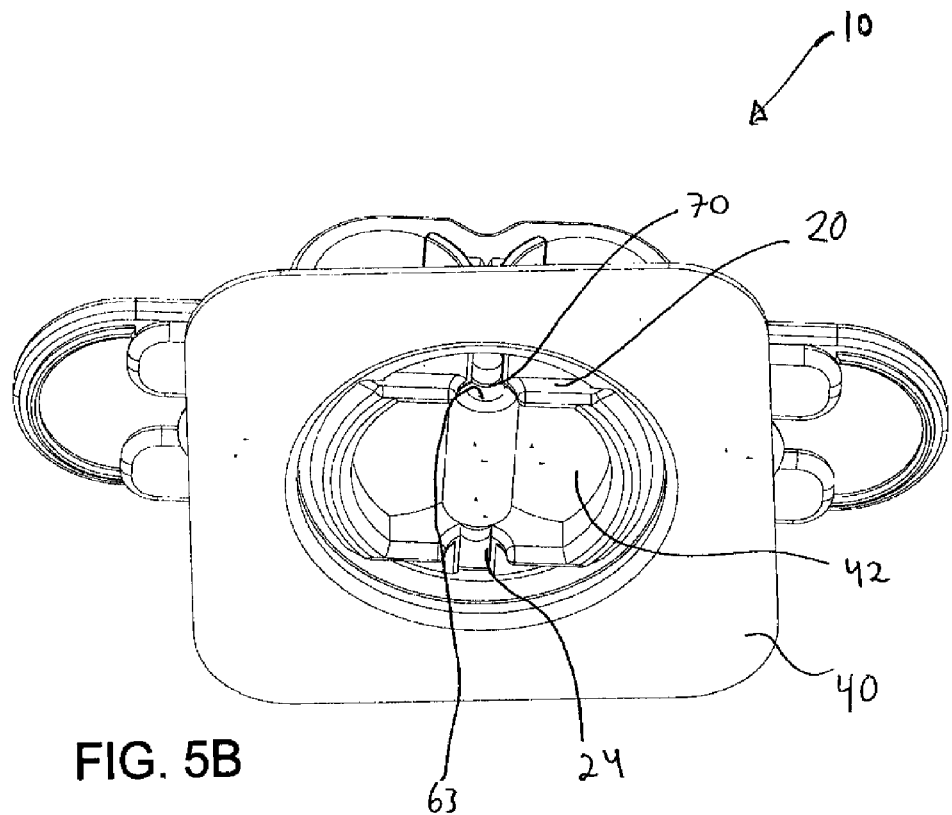
FIG. 5B shows a bottom perspective view of the securing device shown if FIGS. 1 and 2A-2B.

As shown in FIGS. 1 and 5A-5B, in one embodiment the retention strap 50 is connected to the retainer 20 by inserting the central member 60 through the opening 33 (visible in FIG. 1). Once the central member 60 is pushed through the retainer 20 and/or receptacle 42, via opening 33, and is exposed on the underside of the securing device 10, an insertable device, e.g., the pin 70, is inserted into the opening 63. In one embodiment, the pin 70 may have a round diameter and may be held in place by friction after being press fit through the opening 63 (a pin could also include one or more raised crush ribs which serve to hold the pin in a opening 63 by friction). Once the pin 70 is positioned within opening 63, it may be pulled up by central member 60 or pushed up into retention slot 24 and held against the underside of the retainer 20, e.g., by the upward pull of central member 60, which may be somewhat resilient or elastic, or by being snapped or pressed into retention slot 24. At least one end of the pin 70, which may protrude from the end of opening 63, fits against the underside of the retainer 20 within retention slot 24. With the pin 70 in place, the retention strap 50 is securely connected to the retainer 20 and cannot be pulled through the retainer opening 33.

Optionally, the retention strap 50 may be attached to the retainer 20 by welding, gluing, insert molding, taping with some type of adhesive or by any other method or structure suitable for temporarily or permanently attaching the retention strap 50 to the retainer 20. Optionally, the retention strap 50 may be attached to the retainer 20 directly, via an extension of the strap or the retainer, or by any other suitable separate structure.

Referring back to FIGS. 1 and 4A-4B, branching off of the top end 64 of the central member 60 in generally opposite directions are two strap arms 52 which are positioned substantially perpendicular to the longitudinal Y axis of the securing device 10, generally along the lateral X axis, or optionally at an angle, e.g., 1-45° to the longitudinal axis Y. It is contemplated that a single strap arm may optionally be used in certain embodiments.

In one embodiment, each strap arm 52 may extend from the top end 64 of the central member 60, with at least a portion of the strap arm 52 being substantially arc-shaped and the end 53 of the strap arm 52 being substantially linear and/or flat. In another embodiment, the entire strap arm 52 may be substantially linear. Indeed, the strap arm 52 may be configured in any manner or shape suitable for securely holding a catheter device, such as a Foley catheter, against the retainer 20 or receiving area 26. The strap arm 52 may be at least partially flexible or resilient, or may be rigid or stiff. Furthermore, the end 53 of the strap arm 52 may include at least one gripping rib 54 or other suitable structure for creating traction or grip on its top side or underside to allow for ease of gripping, stretching, and/or pulling the strap arm 52 to facilitate attachment and detachment of the strap arm 52 to a retention arm 28. The arched portion 65 or initial portion of the strap arm 52 may optionally include an indentation 66 for receiving the top end of a receiving area 26.

Provided on each strap arm 52 is a latching element. In the embodiment shown if FIGS. 1 and 4A, the latching element is a retention button 57. The retention button 57 may include a substantially flat and/or circular disk shaped end 58 used to attach the strap arm 52 to the retention arm 28, and a substantially flat square-edged end 59 for connecting the retention button 57 to the underside of the strap arm 52 (optionally, the ends 58 and 59 of retention button 57 may be configured or designed in any shape suitable for forming an attachment with the retention arm 52 or retainer 20). Also, the latching element may be attached to the top or bottom surface of the strap arm 52. Connecting the disk-shaped end 58 to the square-edged end 59 is a center column 61 or similar structure. In one embodiment, the square edged end 59 is insert-molded into the strap arm 52, which allows for a stiff retention surface along the end 53 of the strap arm 52.

A retention button 57 may be used to fasten a strap arm 52 to a retention arm 28 in any manner suitable to securely hold the two arms 28, 52 together. For example, the retention button 57 may be slid into the slot 30 or pushed into the retention arm 28, thereby releasably fastening the strap arm 52 to the retention arm 28. In another embodiment (see, e.g., FIGS. 10A-10B), a retention button 453 may be pressed directly into a receptacle 429 opening, or hole in a retention arm 428 and be held by friction. The retention button 453 may also snap or squeeze into the receptacle 429 to form a secure attachment mechanism and to securely fasten the retention strap to the retention arm. Optionally, a separate structure may be used for attaching, latching, fastening, or clipping the two arms together.

Figure 6A:
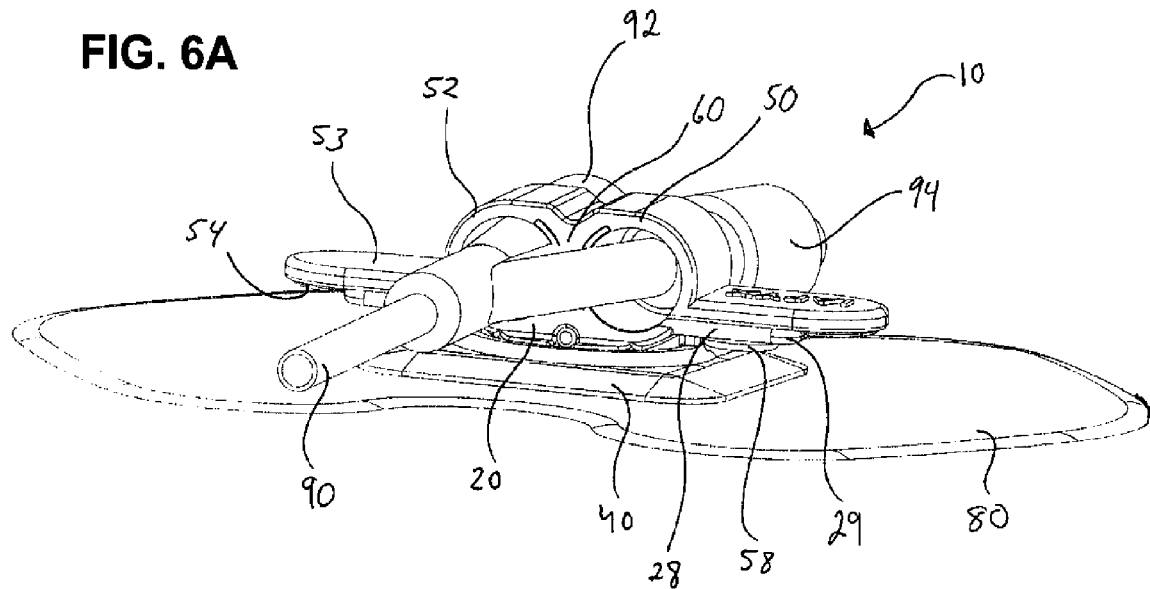
FIG. 6A shows a front perspective view of the securing device shown in FIGS. 1, 2A-2B, and 5, holding a Foley catheter.
Figure 6B:
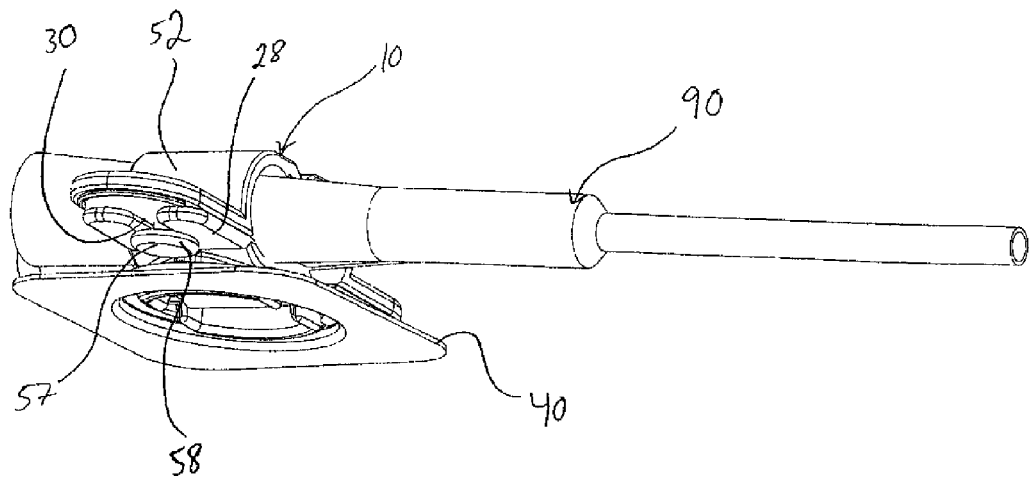
FIG. 6B shows a side perspective view of the securing device shown in FIG. 6A.

Referring to FIGS. 6A-6B, in use, after a catheter 90 has been inserted into a patient, the catheter 90 is placed onto the securing device 10, either before or after the securing device 10 is fastened to a patient. A portion of the catheter tubing is set and/or pressed onto a receiving area 26. In certain embodiments, a receiving area 26 may receive or restrain the catheter 90 and hold the catheter 90 before the strap arm 52 is attached to the retention arm 28.

As shown in the embodiment illustrated in FIGS. 6A-6B, a Foley catheter 90, which may have various shapes or sizes, may be placed onto and/or held by securing device 10 having a retainer 20 with two receiving areas 26. The drainage tube portion 92 of the catheter 90 may be placed and/or held on one receiving area 26 while the inflation lumen 94 of the catheter 90 may be placed and/or held on a second receiving area 26. Once the catheter 90 is in place on the receiving areas 26, a retention strap 50 may be pulled over or around the catheter 90. This may be performed by gripping the gripping rib 54 on the end 53 of the strap arm 52 and pulling and/or stretching the strap arm 52 with sufficient force to extend the end 53 of the strap arm 52 beyond the end 29 of the retention arm 28, such that the retention button 57 may be inserted into the slot 30 (see FIG. 6A).

Upon insertion of the retention button 57 into the slot 30, the top surface of the disk-shaped end 58 engages the bottom surface of the retention arm 28, on either side of the slot 30. Once the retention button 57 begins to enter the slot 30, the tension and/or force exerted on the strap arm 52 is released by releasing the strap arm 52, resulting in the retention button 57 sliding into the slot 30 toward the central member 60. The end 53 of strap arm 52 may also be pushed in the direction of the central member 60 to help slide the retention button 57 fully into the slot 30. The strap arm 52 may optionally be sized such that it can fully accommodate catheters of various sizes without stretching or causing the disk-shaped end 58 to be forced against the underside of the retention arm 28.

Also depending on the size of the catheter or tube secured in the device, the stretched, resilient strap arm 52 may pull on the retention button 57 in the slot 30, forcing the top surface of the disk-shaped end 58 against the underside of the retention arm 28, thereby securely holding the retention button 57 in the slot 30. When a smaller catheter or tube is held or when no catheter is held by the device, the strap arm 52 may pull the disk-shaped end 58 against the underside of the retention arm 28 with less force or it may not pull or force the end 58 at all. The strap arm 52 may optionally be sized such that it can fully accommodate catheters of various sizes with out stretching or causing the disk-shaped end 58 to be forced against the underside of the retention arm 28. The strap arm may optionally be stiff or rigid. Thus, a catheter 90, which may be of various shapes or sizes, can be securely held within the securing device 10 as a strap arm 52 is securely fastened to a corresponding retention arm 28 via the attachment mechanism provided by the interlocking of the retention button 57 and the slot 30.

The securing devices 10 described above as well as the additional embodiments discussed below can be attached to a patient in a variety of ways. As shown in, e.g., FIGS. 2A and 6A, a securing device 10 may include a pad 80, which may be attached to a base 40 or retainer 20. The pad 80 is preferably somewhat flexible to conform to the patient's leg, arm, or other site on the body. The pad 80 may be made of any material suitable to conform to a site on the patient's body, e.g., a hydro colloidal pad. The specific pad shape and size is not limited and various alternatives may be used. The pad 80 in FIG. 2A or 6A is generally rectangular in shape, but could also be a footprint of a retainer or base. The back side of the pad 80 preferably has one or more peelable strips over an adhesive layer or surface. The peelable strips may be removed from the back side of the pad 80, after which the pad 80 may be placed onto a prepared securement site. A cut-out may be provided at the front of the pad 80 to allow the base or retainer to be positioned closer to the insertion or catheter entry point. Alternatively, the securing device 10 may be affixed to a patient by applying adhesive tape around the device and against the patient or an adhesive may be applied directly to the base, trunk or retainer for affixing the device to a patient.

Figure 7A:
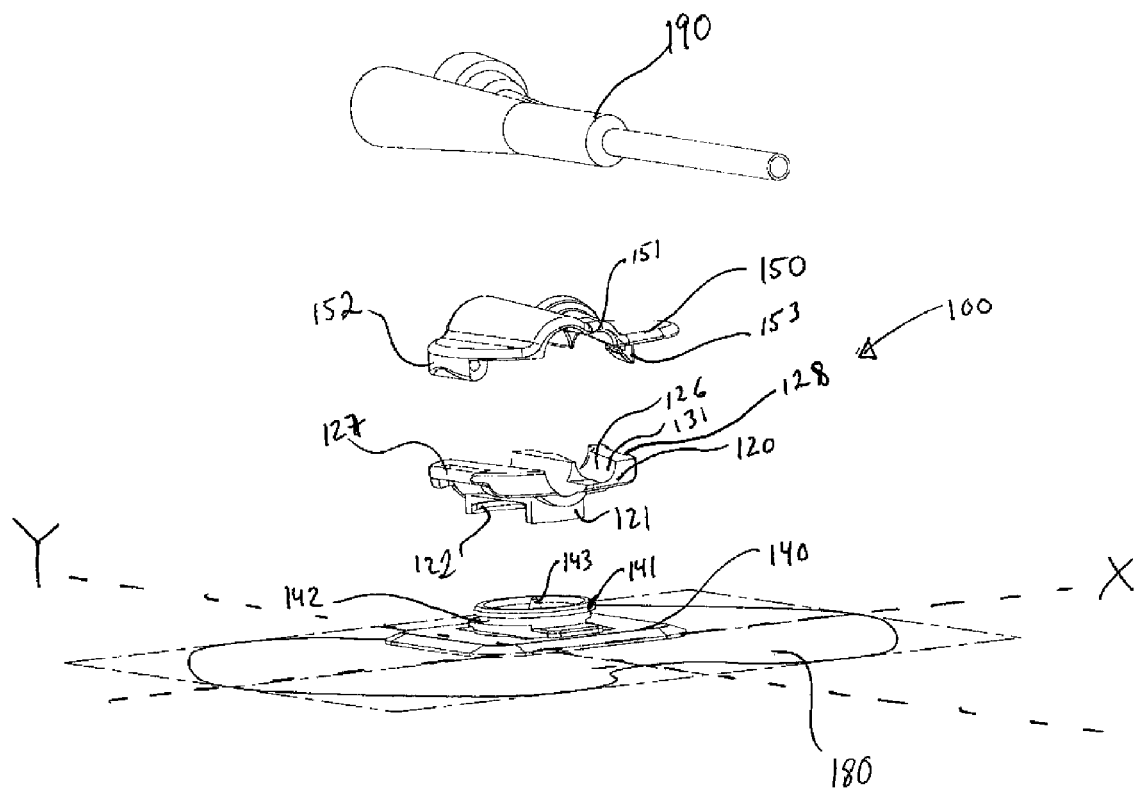
FIG. 7A shows an exploded front perspective view of another embodiment of a securing device.
Figure 7B:
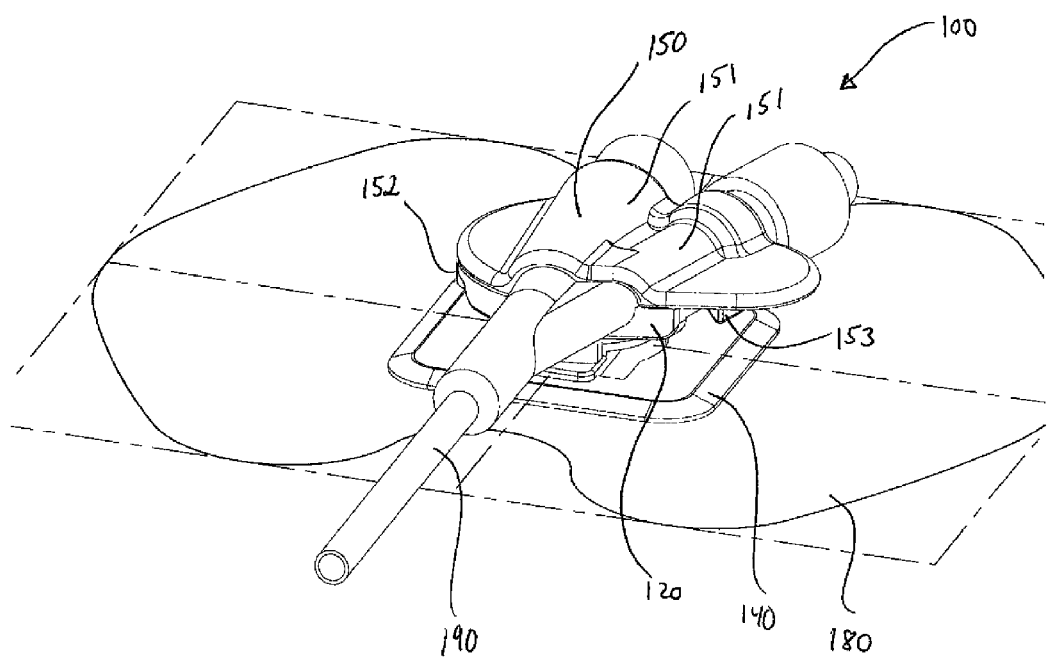
FIG. 7B shows a front perspective view of the securing device shown in FIG. 7A, holding a Foley catheter.

In another embodiment, as shown in FIGS. 7A-7B, a securing device 100 includes a retainer 120 attached to a base 140, and a cover 150 attachable to the retainer 140. The cover 150 may be fastened to the retainer 120 by attaching a hinge 152 of the cover 150 to a hinge latch 127 of the retainer 120. The cover 150 may pivot about the hinge latch 127 to move between opened and closed positions. In the closed position, the cover 150, which includes at least one concave receiving area 151, may rotate down and over top a catheter 190, which may be positioned within a concave receiving area 126 of the retainer 120. In order for the cover 150 to latch into a closed position with the retainer 120, a latching element 153 engages an edge 128 (either of both of which may have an angled surface). The latching element 153 and edge 128 slide past each other, as the latching element 153 flexes outward over the edge 128 and then back to its original position, locking the cover 150 and the retainer 120 together and securely holding or restraining the catheter 190 therein.

In the embodiment of FIGS. 7A-7B, the retainer 120 may be connected to the base 140 with a female-male attachment mechanism. The retainer 120 includes at least one attachment wall 121 having an attachment lip 122. Extending up from the base 140 is a platform 142 (preferably circular) which includes a ridge 141 on its top end and a spike 143, post, pin, or peg extending up from within the center of the platform 142. The retainer 120 is pushed down onto the platform 152 of the base 140 such that an inner surface (which may or may not be angled) of the attachment lip 122 engages against an outer surface of the ridge 141 (which may or may not be angled) and slides over or past the ridge 141 where it latches into place. The spike 143 may help align and center the retainer 120 onto the platform 142 by engaging a hole on the underside of the retainer 120. Other means for attaching the retainer 120 to the base 140 are also contemplated as discussed above with respect to the embodiment of FIG. 1. The base 140 and retainer 120 are preferably attached and configured in a manner suitable to allow for rotational or swivel movement between them. The base 140 is configured to receive the retainer 120, which may be removably or permanently attached thereto. The base 140 may be attached to a pad 180 which may fasten or adhere the device to a patient.

Figure 8A:
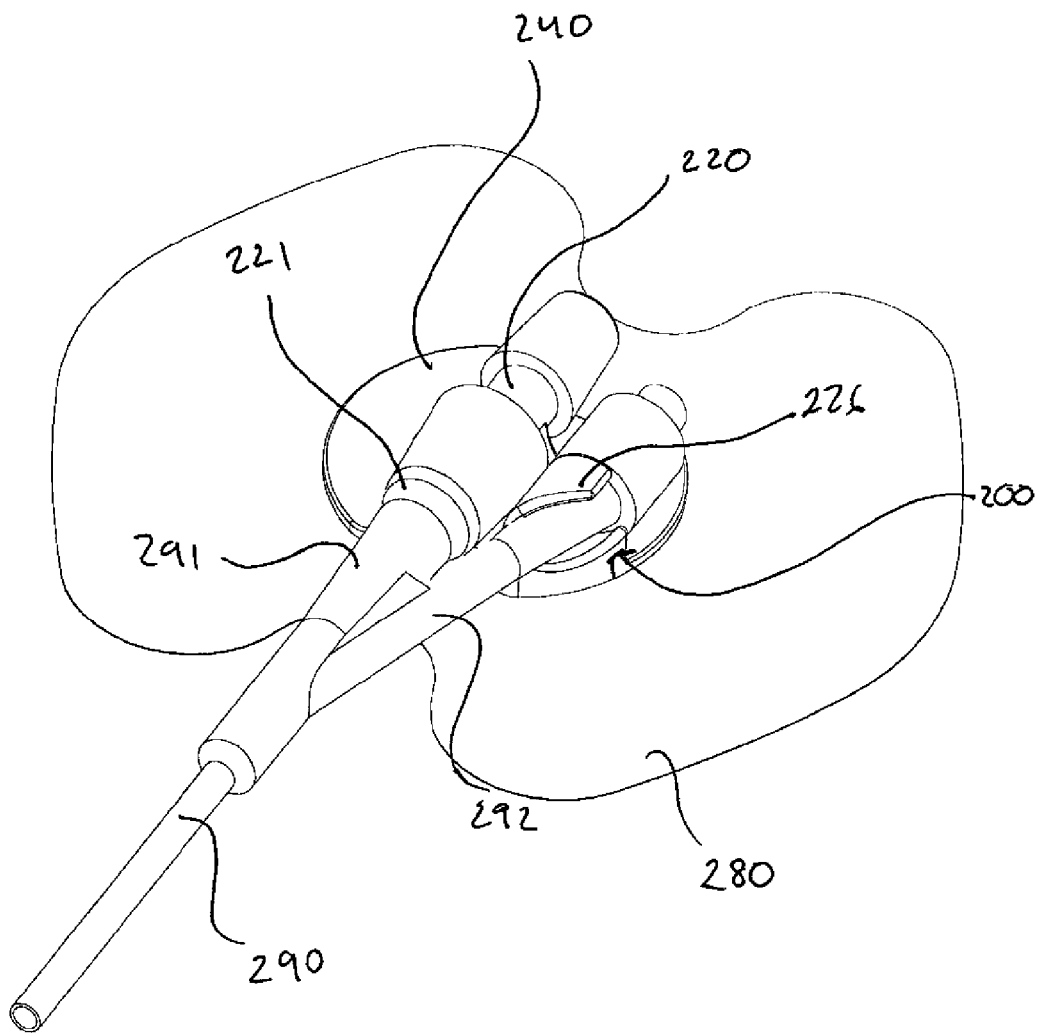
FIG. 8A shows a front perspective view of another embodiment of a securing device.
Figure 8B:
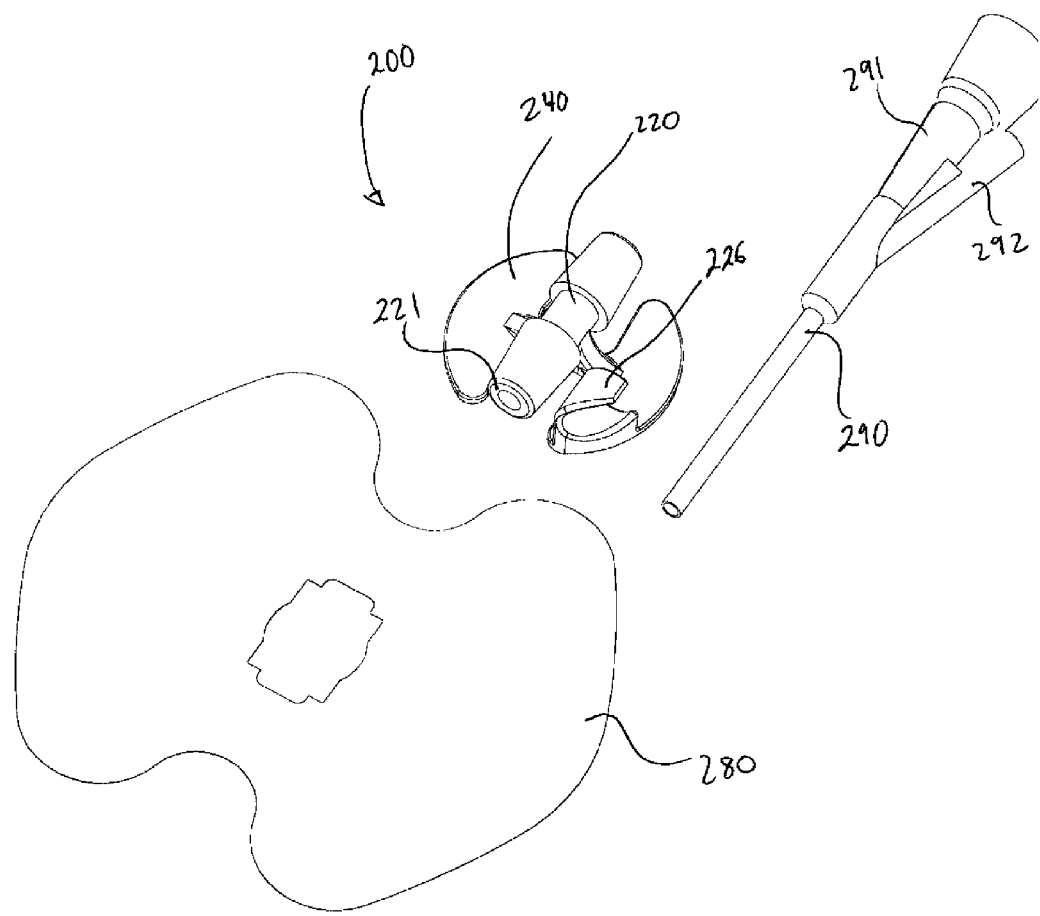
FIG. 8B shows an exploded front perspective view of the securing device shown in FIG. 8A.

In another embodiment, as shown in FIGS. 8A-8B, a securing device 200 may include an adaptor 220 and at least one receiving area 226 positioned adjacent to each other and both extending up from a base 240. The base 240 may be attached to a pad 280. In use, a catheter 190 is placed on said securing device 200 by inserting the inflation lumen 292 into the receiving area 226 and attaching the drainage tube 291 of the catheter 290 to the front end 221 of the adaptor 220. The catheter 290 may be fastened to the adaptor 220 by press fitting the drainage tube 291 into the adaptor 220 where it is held in place by friction or by snapping or screwing the drainage tube 291 into the adaptor 220 to securely hold the catheter in place. The adaptor 220 may also include a barb feature for receiving or attaching catheters, other tubing, or medical devices.

Figure 9A:
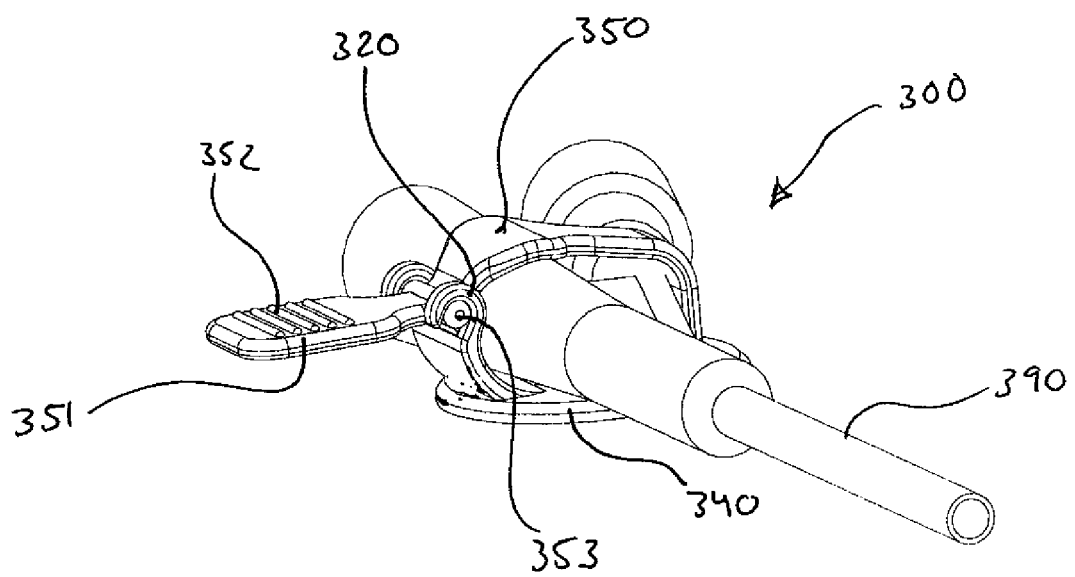
FIG. 9A shows a front perspective view of another embodiment of a securing device holding a Foley catheter.
Figure 9B:
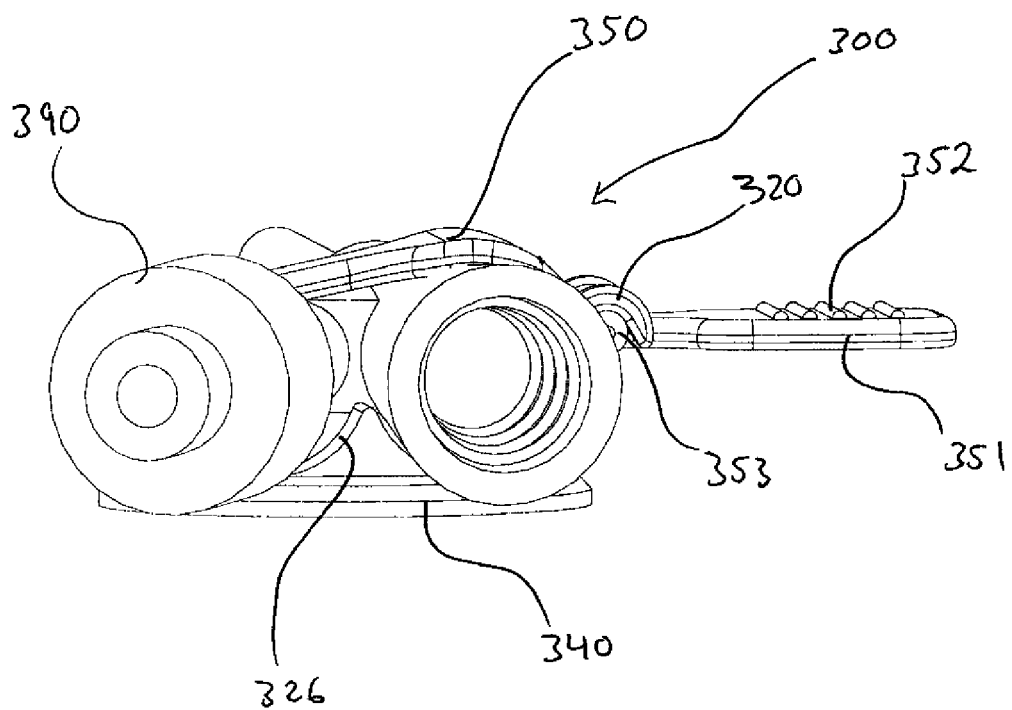
FIG. 9B shows a back perspective view of the securing device shown in FIG. 9A

In another embodiment, as shown in FIGS. 9A-9B, a securing device 300 may include a retainer hook 320 extending from a base 340. At least one receiving area 326 may be provided on the base 340. The securing device 300 also includes a retention strap 350 extending from the base 340 with at least one gripping rib 352 positioned on a top surface or underside of the end 351 of the retention strap 352. The retention strap 350 may also include a bar 353 attached thereto. In use, a catheter 390 is placed within a receiving area 326 (in the embodiment in FIGS. 9A-9B two receiving areas are used) on said base 340. The retention strap 350 is pulled or stretched over or around the catheter 390, by gripping the end 352 of the retention strap 350, such that the bar 353 can engage the retainer hook 320. By releasing the retention strap 350 (which is preferably resilient or elastic), the bar 353 is pulled against the underside of the retainer hook 320, thus securely fastening the retention strap 350 and retainer hook 320 together and securely holding or restraining the catheter 290 within the receiving areas 326 of the securing device 300. Optionally, the retention strap 350 may be fastened to the retainer hook 320 by any suitable structure that latches or fastens the retention strap 350 and retainer hook 320 together with or without the strap 350 or a bar pulling against the hook 320.

Figure 10A:
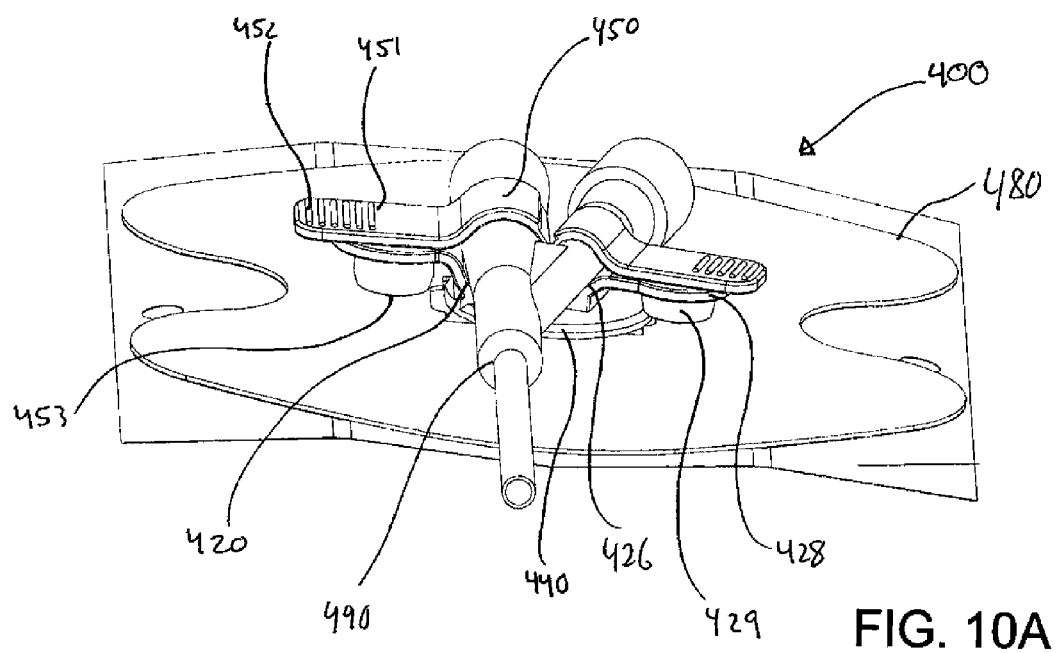
FIGS. 10A-10B show front perspective views of an additional embodiment of a securing device holding a Foley catheter.
Figure 10B:
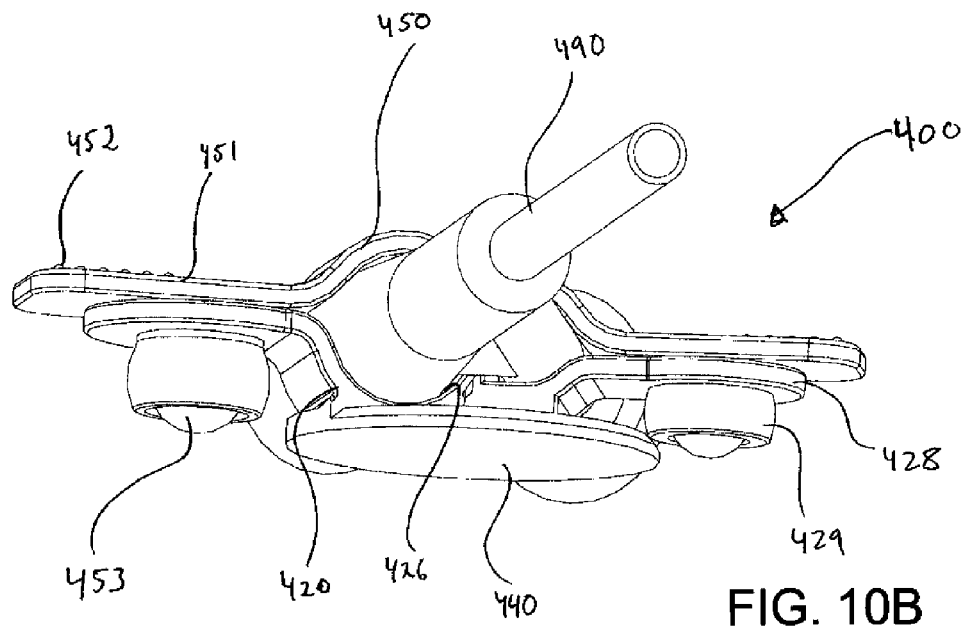

In another embodiment, as shown in FIGS. 10A-10B, a securing device 400 may include a retainer 420 attached (either removably or permanently) to a base 440 which may be attached to a pad 480. The retainer may include at least one retention arm 428 with a receptacle 429 provided off of the end of the retention arm 428 and extending on the underside of the arm. A receiving area 426 may be provided adjacent to a retention arm 428. Extending from the retainer 420 or the base 440 is at least one retention arm 450 having a retention button 453 extending from the underside of the end 451 of the retention strap 450. A gripping rib 452 may be provided on a top surface of the retention strap 450. In use, a catheter 490 is placed on the retainer 420, optionally within a receiving area 426. The retention straps 450 are each pulled or stretched over or around the catheter 490, by gripping the end 451 of the retention strap 450, and the retention buttons 453 are inserted into each receptacle 429. A retention button 453 may snap or squeeze into the receptacle 429 or be held by friction, forming a secure attachment mechanism and securely fastening a retention strap 450 and a retention arm 428 together. This results in the securing device 400 securely holding or restraining a catheter 490 in place.

Figure 11:
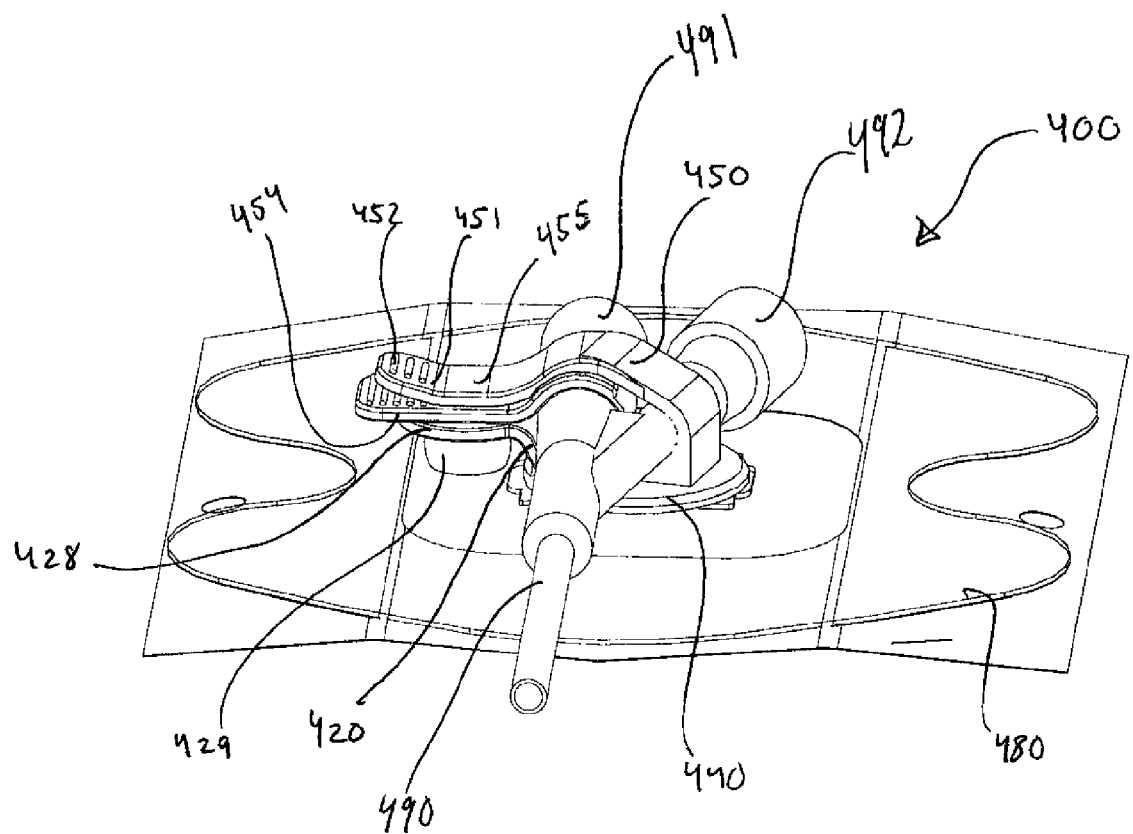
FIG. 11 shows a front perspective view of another embodiment of a securing device with overlapping strap arms.

In the embodiment shown in FIG. 11, the strap arms 454, 455 of the retention strap 450 overlap each other and attach to each other and to a single retention arm 428. That is, a first strap arm 454 extends over the drainage tube 491 of catheter 490 and the retention button of that strap arm 454 is inserted into receptacle 429. Next, the second strap arm 455 may be extended over the inflation lumen 492 of the catheter 490 and onto the first strap arm 454, inserting the retention button of the second strap arm 455 into the retention button (which is also a receptacle) of the first strap arm 454.

Figure 12A:
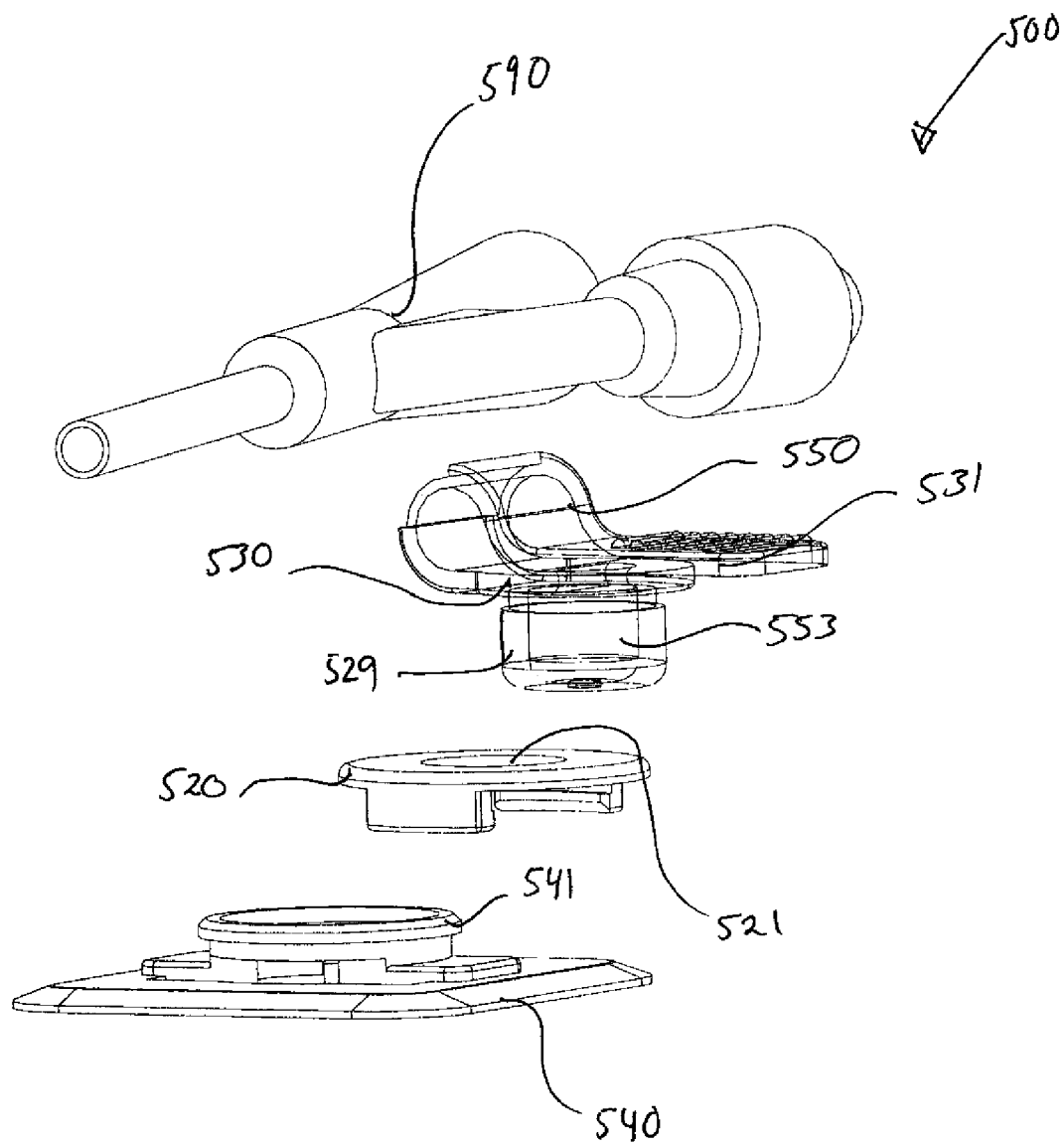
FIG. 12A shows an exploded front perspective view of another embodiment of a securing device.
Figure 12B:
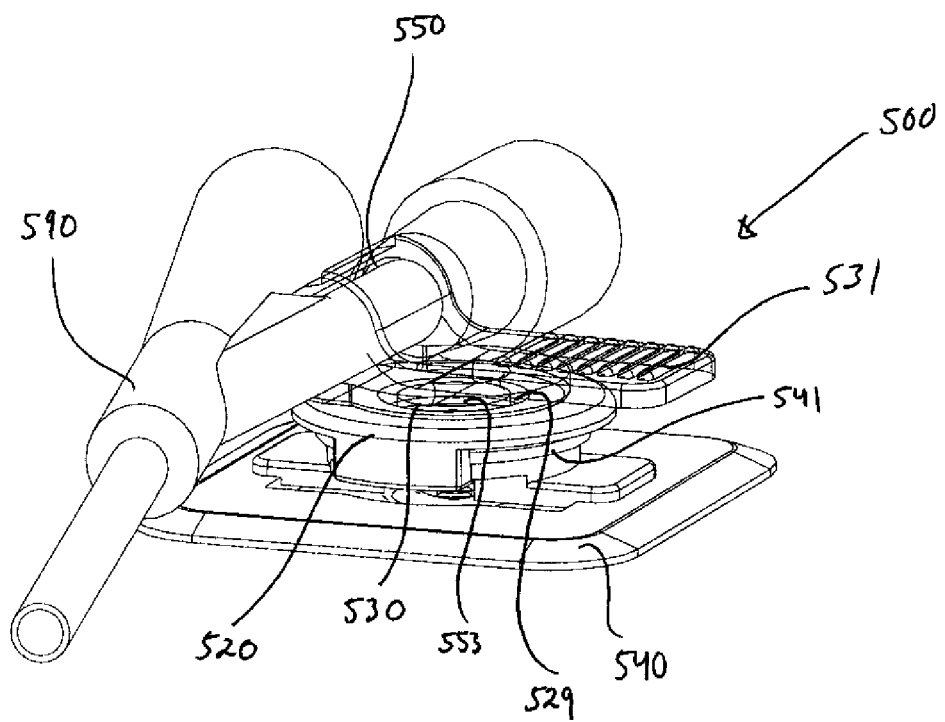
FIG. 12B shows a front perspective view of the securing device of FIG. 12A holding a Foley catheter.
Figure 13:
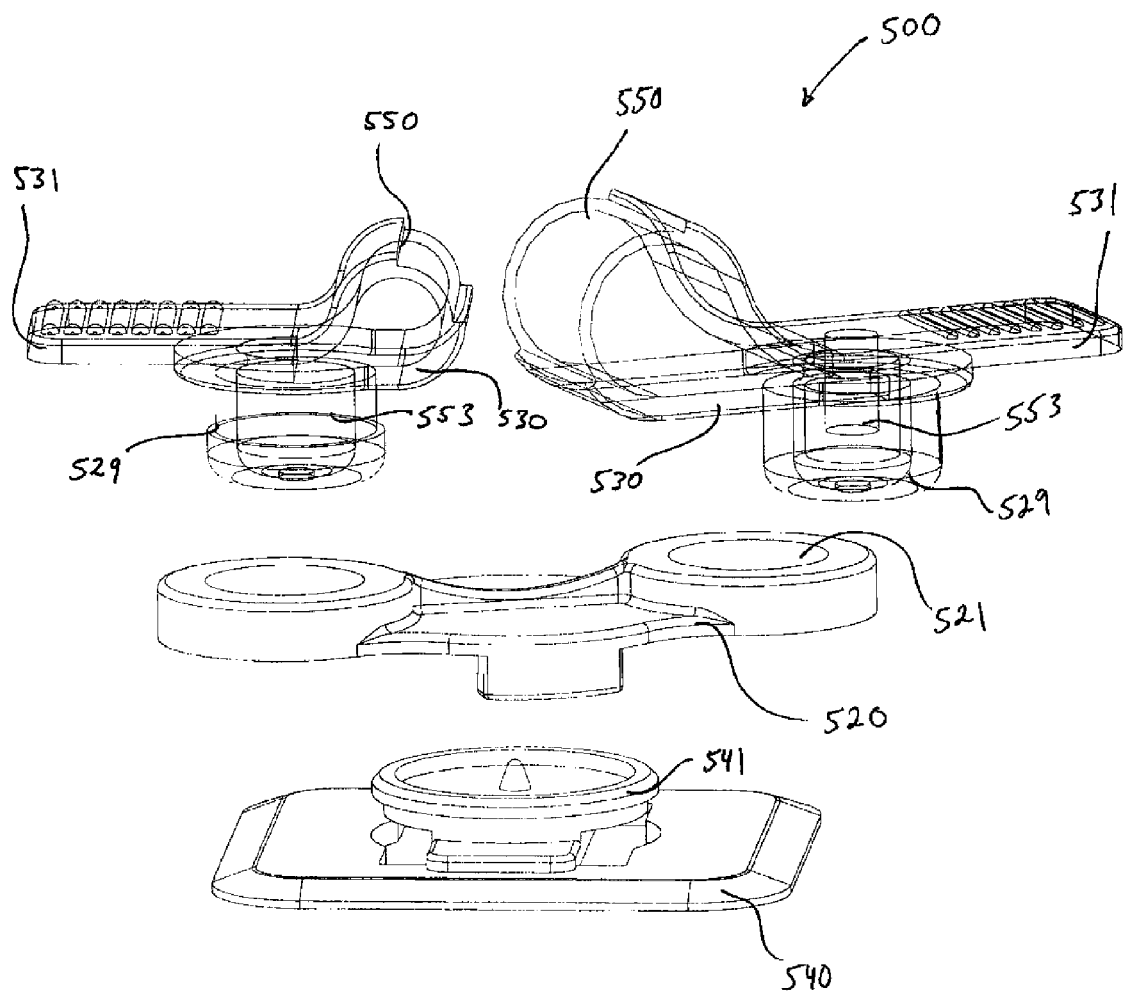
FIG. 13 shows an exploded front perspective view of another embodiment of a securing device.

In another embodiment, as shown in FIGS. 12A-12B, a securing device 500 includes at least one retention strap 550 having a receptacle 529 or other opening on a first end 530 and a retention button 553 extending from a second end 531. The receptacle 529 may fit into the receptacle 521 of a retainer 520 and the retainer 520 may be attached to a platform 541 extending up from a base 540. The retainer 520 may swivel about the platform 541. A catheter 590 may be placed on the retention strap 550 wherein the second end 531 of the strap is wrapped over or around the catheter 590 such that the retention button 553 can be inserted and attached to the receptacle 529 to securely hold the catheter 590 in place. FIG. 13 shows an embodiment as described above having two retention straps 550 and a retainer 520 with two receptacles 521 for receiving the receptacles 529 of the retention straps 550.

Figure 14:
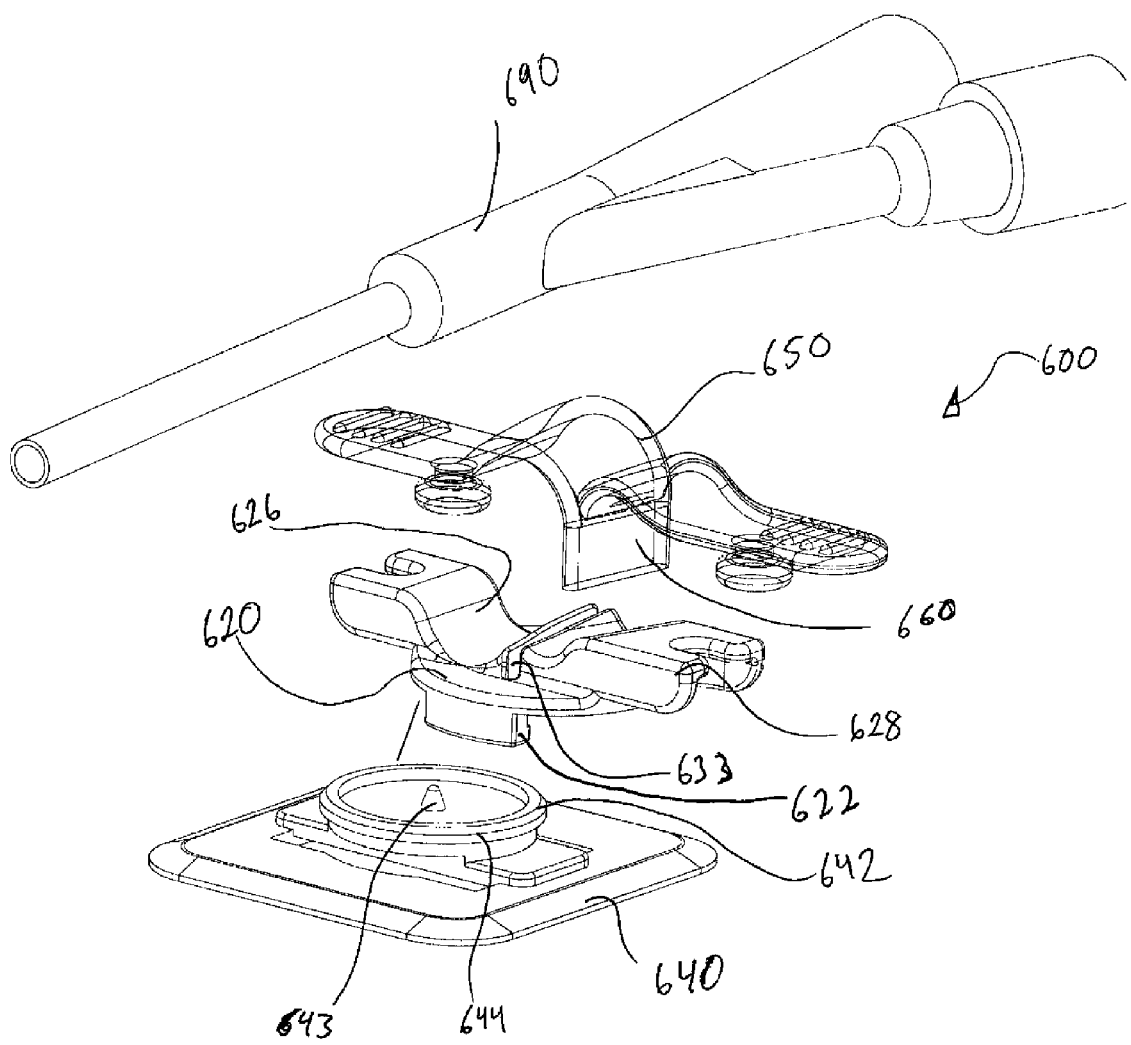
FIG. 14 shows an exploded front perspective view of an additional embodiment of a securing device.
Figure 15:
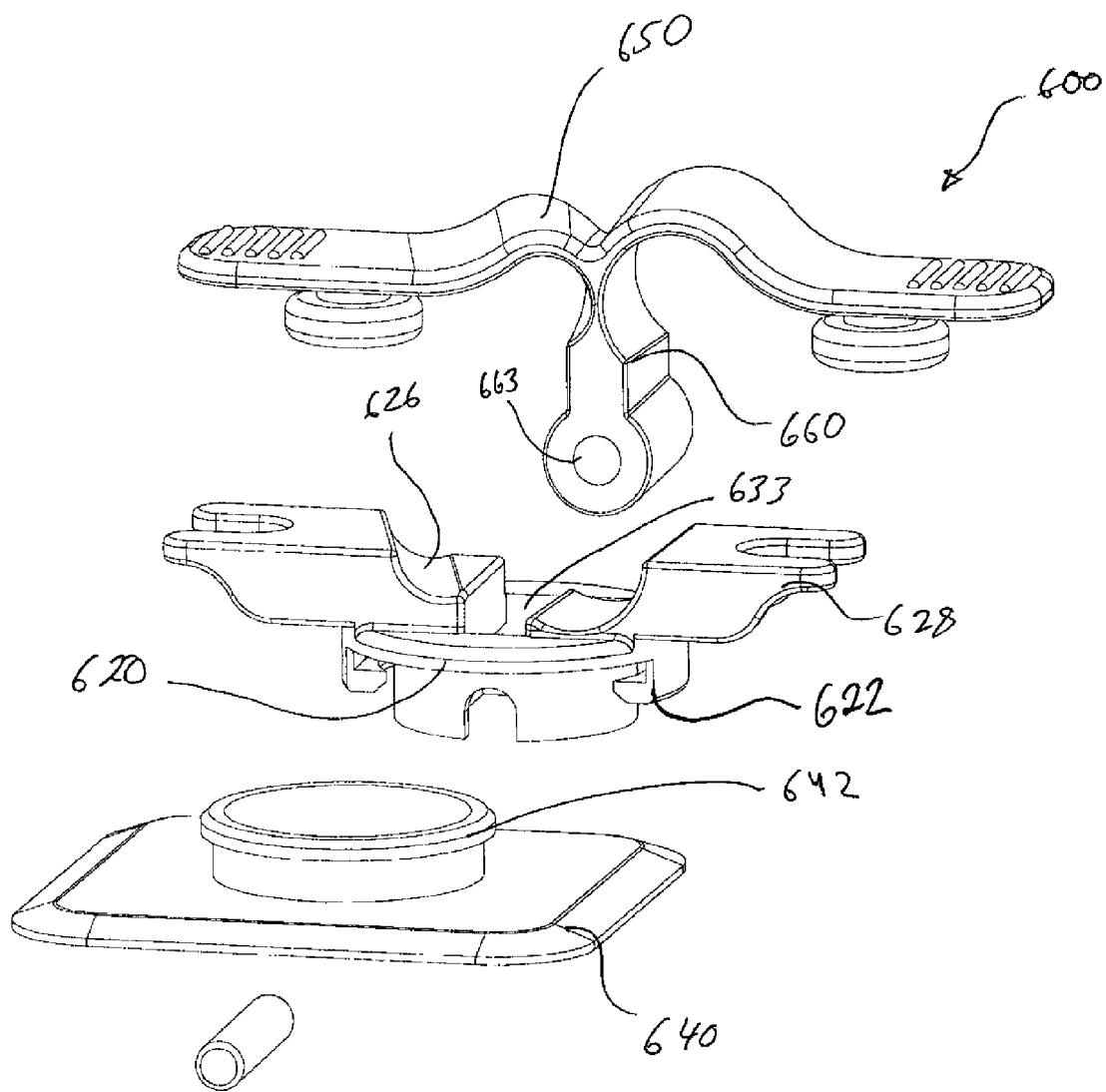
FIG. 15 shows an exploded front perspective view of an additional embodiment of a securing device.

FIGS. 14 and 15 show variations of a securing device embodiment similar to the embodiments described above in FIGS. 1-6. The securing devices 600 have receiving areas 626 with a slightly different orientation than those in the embodiments described in FIGS. 1-6. Retention arms 628 extend from the receiving areas 626 and the receiving areas 626 face a direction generally away from a patient when the device is attached to a patient and are positioned such that a catheter 690 may be set onto the receiving areas 626. Also, the retainer 620 is attached to the outer surface of the ridge 642 of the receptacle, opening, or platform connected to the base 640 as the ridge 642 attaches inside the attachment lip 622 of retainer 620. FIG. 14 shows a spike, post, peg, or pin for aligning and centering retainer 620 onto platform 644. FIG. 14 also shows a retention strap 650 having a central member 660 with no opening (in contrast to FIG. 15, opening 663), which slides into opening 633 and is held in place by friction or any other suitable attaching means.

Any of the securing devices described in FIGS. 7-15 above may be adhered or fastened to a patient by using a pad, which may be made of any suitable material or design as described above with respect to FIGS. 1-6. Alternatively, tape or some other fastening means could be used.

Any of the above-described embodiments and elements described in the embodiment may be used alone or in combination with one another. Furthermore, the securing device may include additional features not described herein. While several embodiments have been shown and described, various changes and substitutions may of course be made, without departing from the spirit and scope of the invention. The invention, therefore, should not be limited, except by the following claims and their equivalents.

The invention claimed is:

1. A device for securing a catheter on a patient, comprising:
a retainer, wherein said retainer has at least one receiving area and at least two retention arms disposed on opposite sides of said receiving area; and
a retention strap removably connectable to said retainer and each of said retention arms by sliding said retention strap along a lateral axis relative to said retainer.

2. The device of claim 1, wherein said retention strap comprises at least one strap arm and at least one latching element connected to said strap arm, and said retention arm comprises a slot.

3. The device of claim 2, wherein said strap arm is attachable to said retention arm by inserting said latching element into said slot, wherein said latching element is forced against an underside of said retention arm while positioned within said slot.

4. The device of claim 1, wherein said retention strap is connected to said retainer by a pin inserted through an opening in said retention strap.

5. The device of claim 1, wherein said receiving area is substantially semicylindrical in shape and configured to receive a catheter.

6. The device of claim 1, wherein said receiving area has an arc shaped perimeter of greater than 180° degree.

7. The device of claim 1, wherein said receiving area is at least partially flexible.

8. The device of claim 1, wherein said retainer is attached to a base in a manner that allows rotational or swivel movement of said retainer relative to said base.

9. The device of claim 8, wherein an adhesive pad is attached to the underside of said base.

10. A device for securing a catheter on a patient, comprising:
a base;
a retainer connected to said base, wherein said retainer has at least one receiving area and at least two retention arms disposed on opposite sides of said receiving area; and
a retention strap removably connectable to said retainer and each of said retention arms, wherein said retention strap comprises at least two strap arms each having a latching element, wherein said strap arms are securely fastened to said retention arms by sliding said latching element along a lateral axis into a slot provided on each of said retention arms.

* * * * *